United States Patent

Mettes

[19]

[11] Patent Number: 5,996,397
[45] Date of Patent: Dec. 7, 1999

[54] REACTIVE GAS SAMPLING/ANALYZING HYGROMETRY SYSTEM

[75] Inventor: Jacob Mettes, New Hope, Pa.

[73] Assignee: Breakthrough Technologies, Inc., Doylestown, Pa.

[21] Appl. No.: 09/033,002

[22] Filed: Mar. 2, 1998

Related U.S. Application Data

[60] Provisional application No. 60/040,087, Mar. 7, 1997.
[51] Int. Cl.[6] .............................. G01N 7/00; B01D 46/00
[52] U.S. Cl. ........................ 73/29.01; 73/24.04; 95/273
[58] Field of Search .............................. 73/64.47, 29.01, 73/24.04; 95/45, 273

*Primary Examiner*—Hezron Williams
*Assistant Examiner*—Jay L. Politzer
*Attorney, Agent, or Firm*—James Creighton Wray; Meera P. Narasimhan

[57] ABSTRACT

The concentration of a component, e.g., moisture, in a sample fluid, such as a chemically reactive gas or liquid, is determined by the creation of an identical concentration in a chemically inert fluid. Sample and inert fluids are brought into contact with each other through a membrane that allows the exchange of the component. The inert fluid's component concentration is varied until it is detected to remain constant after passing the membrane. When the concentration generated in the inert fluid is known, the invention will constitute a quantitative analytical device that does not require the generation of a calibration curve. This means there is no need to generate multiple known component concentrations in the sample material. Alternatively, operating as an alarm device, the detection of a change in concentration in the inert fluid after membrane contact means that the sample's component level is different than that of the inert fluid. In this case the inert fluid concentration is maintained at a fixed concentration corresponding to the maximum allowable or alarm level of the desired component concentration of the sample.

29 Claims, 2 Drawing Sheets

REACTIVE GAS SAMPLING/ANALYZING HYGROMETRY SYSTEM

BACKGROUND OF THE INVENTION

This application claims the benefit of U.S. Provisional application Ser. No. 60/040,087, filed Mar. 7, 1997.

Corrosive gases, such as HCl, become extremely corrosive in the presence of moisture. Therefore, it is desirable to determine the moisture concentration in such gases before exposing products and process equipment to a possibly wet gas. A typical application where very dry high purity gases are introduced to expensive equipment is semiconductor manufacturing. In this industry, particles generated by the corrosive gas ultimately set limits to the level of integration that may be achieved.

Most hygrometers meet with disappointing results when applied to corrosive gases. The corrosive nature of the gas results in the degradation of the interior of the instrument.

In addition, most hygrometers require calibration, meaning that known moisture concentrations have to be introduced regularly into the instrument. That may further enhance corrosion when this needs to be done in the presence of the corrosive gas.

Due to the "sticky" nature of moisture it has always been a difficult component to determine. At low levels it becomes more burdensome and even in non-corrosive gases it is a difficult, time consuming and gas consuming measurement.

Similarity in molecular behavior of moisture and the corrosive matrix gas may also limit the use of certain types of hygrometers. For example, $H_2O$ and HCl are both polar molecules with dew points that are close together in part of the range of interest and therefore, may prove incompatible with some hygrometers.

Currently, in the industry there are several types of commercial hygrometers priced below $50,000 with detection limits as low as 50 parts per billion(ppb). Two widely accepted types are the chilled mirror and the electrolytic cell. No instrument however has gained universal acceptance, and all have limited compatibility with corrosive gases. Recent methods used in corrosive gases are optical in nature with a minimum of components exposed to the gas (ideally only a light beam and a pair of windows). Examples of some methods used, or proposed for use, with corrosive gases are:

Matheson Gas Products, Inc. of East Rutherford, N.J. produces a chilled mirror device, in which the frost point is detected by visual inspection and especially adapted dew point graphs to account for the impact of a corrosive gas. This technique is not a continuous method and works accurately only at relatively high concentrations down to a few parts per million (ppm).

Fourier Transform Infrared (FTIR) spectroscopy approaches the above described ideal. However, to achieve a low detection limit a long path length is necessary which requires a multi pass cell. Such a cell contains mirrors that have to be aligned and that are in contact with the gas. FTIR uses relatively complex, expensive laboratory equipment, requires calibration and is operated by a highly skilled technician.

Diode Laser Spectroscopy, a laser line is locked on a molecular absorption line of $H_2O$ and the attenuation of the laser beam through the gas for a given path length allows computation of the corresponding moisture concentration. Diode laser spectroscopy is a relatively complex, expensive laboratory technique that requires calibration and a highly skilled operator.

Intracavity Laser Spectroscopy is still in a test phase.

That the FTIR, Diode Laser Spectroscopy, and Intracavity Laser Spectroscopy projects are performed by Sandia National Laboratories and are funded through NIST or by government and industry collaboration like SEMATECH illustrate the need to address the above problem. Most projects develop or test a more or less exotic experimental laboratory technique to detect water in corrosive gases.

SUMMARY OF THE INVENTION

The invention allows for the determination of the concentration of a target component in a liquid or gas phase sample fluid. The contact of the sample fluid with the interior of a device, constructed according to the invention, is very limited, which allows for analysis of corrosive, chemically active, toxic, precious or hazardous materials. A configuration according to the invention operates as a quantitative analytical device that does not require calibration by the introduction of samples with known traceable target component concentrations. The invention may also be configured to generate an alarm when a preset upper or lower limit of the target component concentration is breached.

Prior art U.S. Pat. No. 3,367,850, Method and Apparatus for Determining Moisture Content of Hydrocarbon Fluids, uses an exchange device with two separate chambers separated by a membrane. Both chambers have inlets and outlets accommodating a flow of dry inert fluid and a flow of sample hydrocarbon fluid. After an exchange of moisture through the membrane from the sample fluid to the inert fluid the moisture concentration is measured in the inert fluid. The efficiency of the exchange depends on the flowrates of the fluids and the geometry of the exchange device as well as temperature, necessitating a calibration by generating traceable concentrations in the sample fluid.

In the present invention no calibration is required. A controlled flow of wet inert fluid enters the exchange device, while a differential measurement is done to determine the impact of the exchange through the membrane. Detected increase or decrease after the impact of the exchange leads in the present invention to respectively raising or lowering of the entering wetness in the exchange device. When the wetness of the inert fluid is the same at the outlet and inlet, the partial pressures of the wetting material are identical in both the sample and the inert fluid.

A preferred embodiment of the invention comprises a fluid sampling and analyzing apparatus for determining the concentration of a target component in a sample fluid by creating an identical partial pressure of the target component in an inert fluid. The apparatus has an exchange device which has a first and a second chamber. A permeable or perevaporable membrane, which is selectively passable by the target component, but forms a barrier for sample fluid and eventually for the inert fluid, separates the first chamber and second chamber. A target concentration sensor arrangement and a supply of the target component are connected to the first chamber.

The inert fluid flows along side and parallel with the membrane wall in the first chamber of the exchange device, which is equipped hereto with an inert fluid inlet and outlet. The sample fluid is present in the second chamber. When the membrane has a tubular shape, a configuration according to the invention would use the inside of such membrane as the first chamber while the tubing passes through the second chamber, placing the outside of the tubing in contact with the sample fluid. The target concentration sensor arrangement monitors the target component at two or more points in the flow, e.g. upstream and downstream of the membrane. The target component supply is upstream of the target concentration sensor arrangement.

In this embodiment, the target component transfers across the membrane attempting to equalize partial pressures of the target component in the sample and inert fluids. If the target concentration sensor arrangement detects a downstream decrease in partial pressure of the target component in the inert stream after its contact with the membrane, then the partial pressure of the target component in the sample fluid is lower than the partial pressure of the target component in the inert fluid upstream of the membrane. Alternatively, if the target concentration sensor arrangement detects a downstream increase in partial pressure of the target component in the inert stream after its contact with the membrane, then the partial pressure of the target component in the sample fluid is higher than the partial pressure of the target component in the inert fluid upstream of the membrane. When the partial pressure of the target component in the inert fluid remains constant after contact with the membrane, the partial pressure of the target component in the inert fluid equals the partial pressure of the target component in the sample fluid.

A preferred embodiment of the invention has the same configuration as above but also includes an inlet and outlet on the second chamber. The inlet and outlet allow the sample fluid to flow through the second chamber. This flow through the second chamber increases the effectiveness of the exchange device over just circulation in a closed chamber, especially when fresh sample fluid enters the inlet and the direction of the flow in the second chamber is counter to the direction of the flow of the inert fluid at the other side of the membrane. When the membrane has a tubular shape, a configuration according to the invention would use the inside of such membrane as the second chamber while the tubing passes through the first chamber, placing the outside of the tubing in contact with the inert fluid.

The target concentration sensor arrangement may have one or more sensors. With two sensors, target component partial pressure is monitored at two sample positions in the inert fluid stream such that part of, or the whole, membrane is situated in the flowpath between the two sample positions. With one sensor, the same sensor monitors the two sample positions. When using one sensor, a switch arrangement may allow the sensor to alternatively monitor the two sample positions.

Once the target concentration sensor arrangement ceases to detect a difference in the inert fluid's target partial pressures at the two sample positions, it is sufficient to determine the target component partial pressure of the inert fluid in order to know that of the sample fluid. The inert fluid's target component partial pressure may be measured directly by the target concentration sensor arrangement which preferably consists of sensors that are specific and calibrated. A sensor is specific when it possesses sufficient selectivity towards the target component against possible traces of sample fluid or other components present in the inert fluid. Calibration here means calibration for use in the inert fluid which requires in most cases the creation of a calibration curve.

Alternatively, the target component concentration in the inert fluid may be determined from knowledge regarding the size of the target component addition (e.g. in ng/minute) and the flow rate of the inert fluid (scc./minute) provided that this stream is free of the component before the addition. In this case, the invention constitutes a quantitative analytical device that does not require calibration by generating streams of fluids with known traceable concentrations of the target component.

A preferred embodiment includes a feedback controller which connects the target concentration sensor arrangement to the supply of the target component. The feedback controller receives and interprets the signal from the target concentration sensor arrangement and provides signals to the target components supply that control the rate at which the supply adds or removes target component to or from the inert fluid stream.

The feedback mechanism adds target component at an increased rate when the target component concentration increases after membrane contact. Alternatively, a detected decrease results in a decreased addition rate.

A preferred embodiment for a method for measuring the concentration of a target component in a sample fluid comprises providing an exchange device having a first and a second chamber and a permeable membrane between the first and second chambers. An inert fluid flows through the first chamber while a sample fluid is present in and eventually flows through the second chamber. To control the concentration of the target component in the inert fluid a supply of the target component is connected to the first chamber. The permeable membrane transfers target component from the first chamber to the second chamber and vice versa. The net effect of the transfer is that target component moves from the fluid with the higher partial target component pressure to the fluid with the lower partial component pressure. To measure the concentration of the target component in the inert fluid, a target concentration sensor arrangement is connected to the first chamber. The supply of the target component is connected upstream of the target concentration sensor arrangement. The concentration of the target component in the inert fluid is regulated until the concentration in the inert fluid passing through the first chamber remains constant. This method applies a succession of concentration measurements and corrected supply rates until the partial pressure in the inert fluid approaches the partial pressure in the sample fluid. The method may be applied continuously which allows to monitor changes in the sample fluid's target component concentration over time.

The effectiveness of the method may be affected by a difference in the temperature and pressure of the inert fluid and that of the sample fluid. A pressure gradient across the membrane influences the movement of the target component as well as possibly traces of sample fluid across the membrane. Operating the sample fluid at a higher pressure than the inert fluid has the advantage of a higher target component partial pressure and consequently a larger signal from the target concentration sensor arrangement. However, such condition could increase the sample fluid traces in the inert fluid. A preferred embodiment includes regulating the pressure of the inert fluid and the sample fluid by using back pressure regulators or similar devices in the art. A preferred embodiment includes venting one or both of the fluid streams that pass through the exchange device into atmospheric pressure placing flow control means upstream of the exchange device. This assures a good stability of the pressure and equality when venting both streams this way. This is possible for non-specific sensors such as those placed in a Wheatstone bridge based on thermal conductivity (TCD) or gas density (GADE) or for a single detector such as the electrolytic phosphoric acid cell specific for moisture.

Similarly, a temperature gradient may influence the movement of components across the membrane. Therefore, another preferred embodiment includes regulating the temperature of the inert and sample fluids by using a heater or refrigerator.

A preferred embodiment for a method for monitoring if the concentration of a target component in a sample fluid is within a certain range comprises providing an exchange device having a first and a second chamber and a permeable membrane between the first and second chambers. An inert fluid flows through the first chamber while a sample fluid is present in and eventually flows through the second chamber. To regulate the concentration of the target component in the inert fluid to a desired constant value a supply of the target component is connected to the first chamber. The permeable membrane transfers target component from the first chamber to the second chamber and vice versa. The net effect of the transfer is that target component moves from the fluid with the higher partial target component pressure to the fluid with the lower partial component pressure. To measure the concentration of the target component in the inert fluid a target concentration sensor arrangement is connected to the first chamber. The supply of the target component is connected upstream of the target concentration sensor arrangement. Then observe the direction of the concentration change of the target component in the inert fluid after membrane contact. An increase in concentration means that the partial pressure in the sample fluid is higher than the fixed partial pressure in the inert fluid. A decrease means a lower partial pressure in the sample fluid. The detection of an increase triggers an alarm in case the method is used to monitor if a certain maximum allowable level is exceeded. Similarly, the method may be used to indicate when the concentration is less than a certain minimum.

This method is a continuous process of indication if a concentration is above or below a certain level. As soon as the concentration in the downstream inert fluid ceases to be lower than in the upstream fluid, an alarm will be given allowing to check, e.g. that the level of a contaminant in a process fluid is below a specified level. Similarly, as soon as the concentration in the downstream inert fluid ceases to be higher than in the upstream fluid, an alarm may be given allowing to check the presence of a minimum required level of a process component.

The effectiveness of the method may be affected by a difference in the temperature and pressure of the inert fluid and that of the sample fluid. A pressure gradient across the membrane influences the movement of the target component as well as possibly traces of sample fluid across the membrane. Operating the sample fluid at a higher pressure than the inert fluid has the advantage of a higher target component partial pressure and consequently a larger signal from the target concentration sensor arrangement. However, such condition could increase the sample fluid traces in the inert fluid. A preferred embodiment includes regulating the pressure of the inert fluid and the sample fluid by using back pressure regulators or similar devices in the art. A preferred embodiment includes venting one or both of the fluid streams that pass through the exchange device into atmospheric pressure placing flow control means upstream of the exchange device. This assures a good stability of the pressure and equality when venting both streams this way. This is possible for non-specific sensors such as those placed in a Wheatstone bridge based on thermal conductivity (TCD) or gas density (GADE) or for a single detector such as the electrolytic phosphoric acid cell specific for moisture.

Similarly, a temperature gradient may influence the movement of components across the membrane. Therefore, a preferred embodiment includes regulating the temperatures of the inert and sample fluids by using a heater or refrigerator.

With some membrane materials, traces of inert fluid material may pass through the membrane and enter into the sample fluid. This does not pose a problem where the sample fluid is used only for analysis or when inert fluid material contamination is harmless for further use of the sample fluid.

The membrane may be highly resistant to chemical attack, e.g. when the sample fluid is chemically reactive. Suitable membrane materials include Teflon, Nylon and ion-containing polymers or ionomers such as perfluorosulfonate ionomer (Nafion), ethylenes, styrenes, rubbers, and those based on poly(tetrafluoroethylene) in case the target component is moisture. Other candidates include well-known semipermeable membranes such as polyvinyl chloride, cellophane (cellulose acetate), tracing cloth, etc. The membrane and stream control means are the only components in contact with the sample fluid. When the sample fluid is not chemically reactive, other materials may be used for the membrane. The potentially delicate sensors are only exposed to the inert, non chemically reactive, fluid.

The further discussed selectivity of the membrane guarantees that only non-damaging trace amounts of the sample fluid material pass into the inert fluid. The membrane allows the passage of the component and forms a barrier for the corrosive sample fluid.

Transport mechanisms through the membrane may include, but are not limited to permeation and perevaporation. Permeation is a diffusion process where the membrane transports the component much more efficiently than the sample fluid. This is illustrated by the large differences in the permeability of (teflon) fluorocarbon resin FEP, at 23 degrees C., for water, NaOH vapor and $H_2SO_4$ vapor, respectively 0.09, $4\times10^{-25}$ and $8\times10^{-6}$ [gm/100 $in^2$/24 hrs.mil ].

An alternative to permeation is perevaporation when using, e.g. Nafion tubing which is very selective toward moisture. In perevaporation, the Nafion wall material absorbs, in a fast first order kinetic reaction, water from a wet gas inside the tubing as water-of-hydration. The process is completed when such absorbed water evaporates at the outside of the tubing into a dry purge gas. Where the component is water vapor and the sample fluid consists of gas phase HCl, a material such as Nafion passes the moisture very selectively and has the above mentioned chemical resistance to the reactive sample fluid.

Applied to the drying of gases, membrane devices such as manufactured by Perma Pure may be modified for use in the exchange device in the invention. Hereto, the device's tubular Nafion membrane, that passes the sample fluid, is surrounded by a stainless steel electropolished tube. The inert fluid stream passes between the Nafion tube's outside wall and the inside wall of the electropolished stainless steel tube. The electropolished stainless steel tube may closely surround the tubular membrane to assure good surface contact of the membrane with a locally fast flowing inert fluid. The inert fluid's inlet and two sample point connections to the target concentration sensor arrangement of the exchange device are made with all metal, e.g. VCR, fittings and are teed in the electropolished stainless steel tube at a short distance of the tube's extremities. The two extremities of the tubular membrane and that of the electropolished stainless steel tube, the so called "shell", come together in heat exchanger type fittings such as supplied by Perma Pure for its driers. In such heat exchange fittings, the membrane is connected by means of an "O" ring, which potentially may contaminate the inert fluid. A flow of inert fluid directed toward such "O" ring may exit through the heat exchange type connector's shell ports, reducing such contamination while purging the shell volume at the extremities of the membrane which may house a pressure gauge and a temperature sensor.

A preferred embodiment has an exchange device as the above described adaptation of the Perma Pure dryer. This embodiment connects a backpressure regulator to the shell port of the heat exchange type connector at the extremity of the membrane where the inert fluid enters the shell. This backpressure regulator will maintain the pressure of the inert fluid inside the first chamber of the exchange device by adapting the flowrate of inert fluid passing through it. The shell port of the heat exchange type connector at the other extremity of the membrane is equipped with a flow restriction such as a needle valve or calibrated orifice. Fluctuations in flowrate of the inert fluid entering the first chamber will only impact the flow of inert fluid in between the point of entry of the inert fluid into the first chamber at a short distance from the membrane's extremity and the backpressure regulator at the shell port. This way, the flowrate of inert fluid inside the first chamber between the two sample positions of the target concentration sensor arrangement will stay constant and will not be affected by fluctuations in the flowrate of incoming inert fluid into the first chamber. Differences in target component addition upstream of the point of entry of the inert fluid into the first chamber can cause such fluctuation in flowrate.

The choice of inert gas will be dictated by its impact on the sensor, cost, availability and also by considerations described hereafter. Even in the case of perfect stream control means, there is still the fact that the natures of the fluids on the two sides of the membrane are different. Even in the absence of a gradient in component concentration, such difference in fluids, by itself, may cause some component transport. For example, there is a three times greater permeation rate for atmospheric oxygen into helium than into nitrogen. This difference is seen in two gases that are extremely different in nature, and there is no quantitative explanation for the observed phenomenon.

Such an effect results in only a small percentage of offset that may be determined with calibration samples. It may even be compensated for by deliberately maintaining a certain temperature or pressure gradient over the membrane to counteract the offset.

The sensor does not need to be calibrated in order to detect the direction of a difference in concentration between the two indicated positions in the inert fluid stream. It is sufficient that the sensor's signal as a function of the concentration either rises or descends in a monotone fashion in the range of interest.

The target concentration sensor arrangement does not have to be specific to the component, provided it is sufficiently insensitive to the level of trace amounts of sample material present in the inert fluid. In such case, a very sensitive sensor like API (Atmospheric Pressure Ionization) may be used in the arrangement, but otherwise, the more selective APIMS (Atmospheric Pressure Ionization Mass Spectrometer) is preferable. A preferred sensor is an oscillating quartz crystal equipped with a hygroscopic layer, which signal output corresponds with the crystal's resonance frequency. Sensors based on chopped dual beam nondispersive IR are also preferable for detecting a component difference as well as a bridge based on thermal conductivity (TCD) or Gas Density.

The requirement that the sensor be specific less stringent when one compensates for the presence of trace amounts of sample fluid in the inert stream. The concentration of such trace amounts is stable during operation and may be taken into account when it causes a constant stable offset over the operating range of the sensor, easily applicable to detectors such as TCD and GAPE, by zeroing the bridge. Trace amounts of sample fluid in the inert fluid may also be compensated for by adding to the flow from the upstream sample point in the exchange device toward the sensor the same concentration of sample fluid as is added by membrane contact to the flow from the downstream sample point toward the sensor.

A preferable target concentration sensor arrangement is one which uses two sensors, one upstream and one downstream of the exchange device. Positioned in the inert fluid, before and after the exchange device, two sensors detect any change in component concentration after membrane contact. Such setup may use slower sensors but need better repeatability, offset and span calibration than when using a single sensor in the target concentration sensor arrangement.

A switching arrangement to switch periodically between the sample gas and a blank zero gas is used in certain type of hygrometers. Pressure may be used to do the actual switching avoiding valves in the critical areas of the flow path. Such pressure switch arrangement is also found in chromatography setups. Pressure switching is advantageous in the case of a "sticky" molecule like moisture because it avoids dead volumes where the flow is stagnant and, instead of interrupting, it changes the direction of the flows. The use of a pressure switch is described in more detail in the preferred embodiment of the invention.

In many situations, compressed air may be chosen as the material for the inert fluid. The compressed air has to be dried in the case that the invention is used as a hygrometer. Extremely pure nitrogen and argon gases may be generated by the distillation of liquified air. originating from the vaporization of a cryogenic source, the moisture content may be at the parts per billion level. Such gas is available in many analytical laboratories as well as many industrial sites, such as semiconductor manufacturers, where it is used as a process gas. Dry nitrogen is often available in the industry as purge gas, used prior to exposing equipment to a corrosive gas.

The invention need not always be used to analyze reactive or corrosive gases. Another reason for its application is the need to preserve sample or to avoid calibrated samples. In such situations, the inert fluid material may be identical to that of the sample, which eliminates the potential problem caused by different fluid materials mentioned above. When a stream of sample fluid is available, that stream may also be used as inert fluid after removal of the target component.

The described invention is very applicable to "on line" measurements, in which the apparatus continuously equalizes, for example, the water concentration in the inert fluid to that of the (corrosive) sample gas. A slip stream teed off from a process stream may be used for the analysis in which case the stream that exits the analyzer is discarded. Alternatively, the process stream itself may pass through the analyzer. In this last arrangement it is critical not to contaminate the process stream. The slip stream arrangement is preferable if traces of inert fluid material entering into the process stream pose an undesirable contamination risk to the process.

It is possible to pass the membrane tubing through the inside of a reservoir of sample material. The inert fluid flows inside the tubing, while the contact with the sample material takes place at the tubing's outer wall. Renewal of material after membrane contact in the sample fluid takes place through turbulence. The renewal is relatively slow which is acceptable because the component concentration in a reservoir remains constant over longer periods of time.

The above illustrates that the sample material consumption may be as low as zero. In general the consumption of sample material needed for proper operation depends on factors like the sensitivity and speed of response of the sensor as well as material, length and thickness of the membrane. Low gas consumption is of importance when measuring on individual gas cylinders, especially when the sample material is precious or hazardous.

The fact that no calibration curve has to be created, which requires the generation of known traceable concentrations in the sample material, is a reason to apply the instrument when the sample is precious, dangerous, radioactive or toxic. The fact that the sample is only in contact with the membrane is another reason to apply the instrument. The latter allows for recycling the sample material back into a process stream or into its container. The process may also recycle the sample or inert material, such as Helium in case of a TCD, by compressing it after it exits the analyzer and feeding it back to the analyzer's inlet. In this last arrangement an all metal pump may be used to assure contamination free operation.

These and further and other objects and features of the invention are apparent in the disclosure, which includes the above and ongoing written specification, with the claims and the drawings.

DETAILED DESCRIPTION OF SOME PREFERRED EMBODIMENTS

Figure 1:
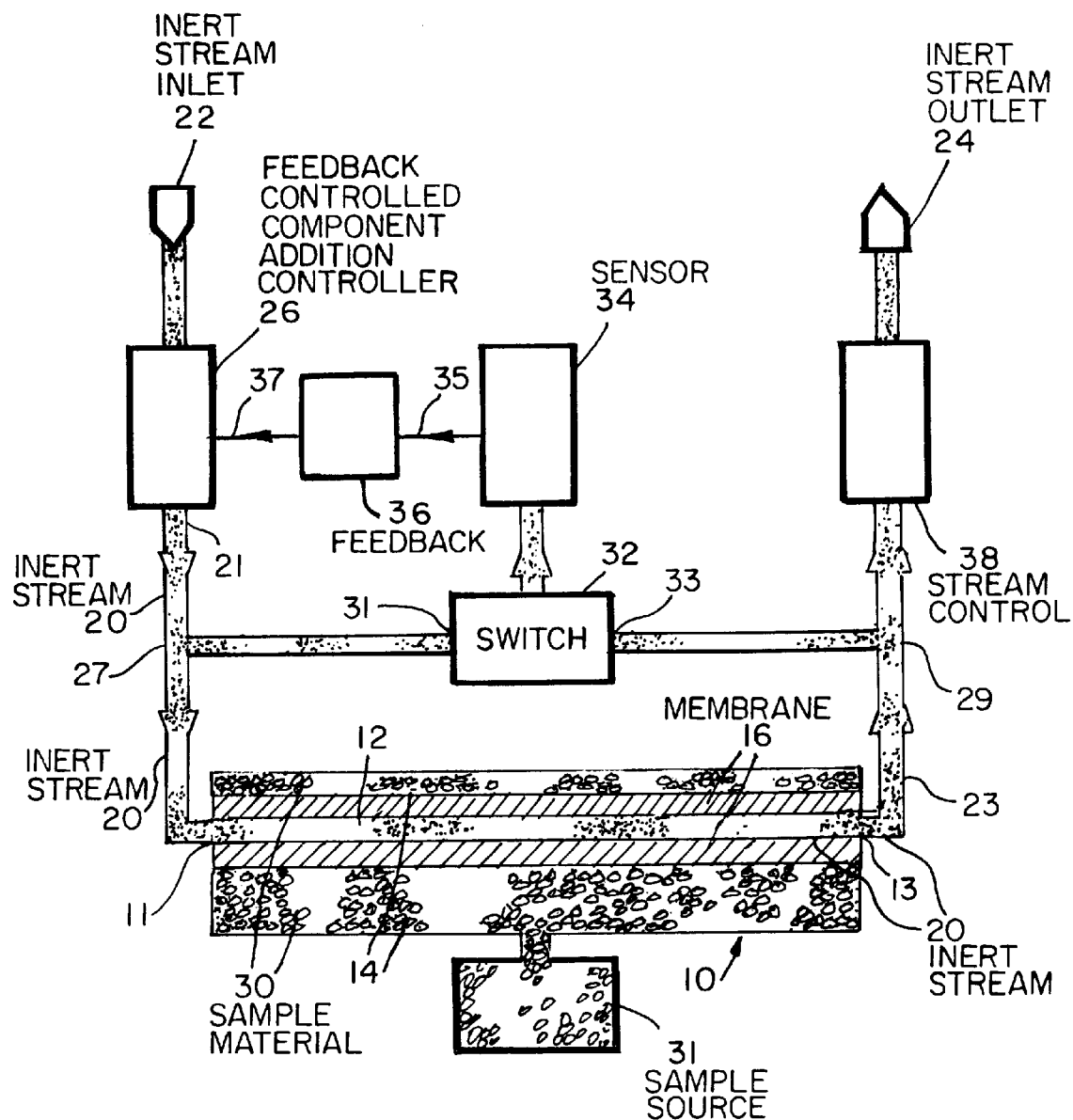
FIG. 1 is a schematic drawing of a preferred embodiment of the invention.

FIG. 1 is a schematic drawing of the invention showing "black box" drawings for the different elements of a preferred embodiment of the invention. The component exchange device 10 consists of a first chamber 12 and a second chamber 14. A membrane 16 separates the first chamber 12 and second chamber 14.

The inert stream 20 flows through the first chamber 12, and the sample material 30 from a sample source 31 is present in the second chamber 14. Only target component transfers between the inert stream 20 and the sample material 30 across the membrane 16, while such transfer is selectively blocked by membrane 16 for sample and inert stream material.

After entering inert stream inlet 22, the inert stream 20 is directed into feedback controlled component addition 26, where target component is added to inert stream 20. Before entering into the inlet 11 of the first chamber 12 of exchange device 10, part of the stream 21 that exits feedback controlled component addition 26 is teed off 27 to flow to one inlet 31 of the two inlets of switch arrangement 32. The other inlet 33 of switch arrangement 32 receives inert stream 20 material teed off 29 downstream 23 at the outlet 13 of first chamber 12 of exchange device 10. The remainder of the inert stream 23 that exits 13 first chamber 12 of the exchange device 10 flows into stream control 38 whereafter it exits through inert stream outlet 24. The switch arrangement 32 alternates connecting the inert stream 20 teed off 27 upstream 21 of first chamber 12 and the inert stream 20 teed off 29 downstream 23 of chamber 12 to the sensor arrangement 34 that monitors this way the target component concentrations on these two streams.

A feedback mechanism 36 takes as its input signal 35 the output from sensor 34 together with information regarding which of the two streams, the inert stream 20 teed off 27 upstream 21 of first chamber 12 or the inert stream 20 teed off 29 downstream 23 of first chamber 12 is connected to the sensor 34. The feedback mechanism 36 interprets this signal and information and provides a signal 37 to the feedback controlled component addition 26 to control the amount of target component introduced by feedback controlled component addition 26 into the inert stream 20 at its exit 21.

In operation, sample fluid 30 is placed in the second chamber 14, and an inert stream 20 flows through the inert stream inlet 22, passes through feedback controlled component addition 26, flows into the first chamber 12 where it comes into contact with membrane 16, and leaves through the inert stream outlet 24 after passing through stream control 38. The inert stream 20 contains a regulated concentration of the target component. As the inert stream 20 and the sample material 30 are both in contact with the membrane 16, target component is exchanged between the two flows through the membrane 16. The net effect is for the target component to move from the fluid 20 or 30 with the higher target component partial pressure to the fluid 20 or 30 with the lower target component partial pressure. The sensor arrangement consisting in this case of switch 32 and sensor 34 detects changes in target component concentration in the inert stream 20 upstream 21 and downstream 23 from the exchange device 10.

Before the inert stream 20 enters the exchange device 10, target component is added to or removed from the inert stream under the control of the feedback mechanism 36. The basic measurement takes place in the inert stream 20 by the sensor arrangement that provides a signal 35 that corresponds to the difference in the target component concentration upstream and downstream of the exchange device 10. The inert stream's 20 target component concentration is adapted until the concentration in the inert stream 20 does not change after contact with the membrane 16.

A stream control 38 may consist of a backpressure regulator that in combination with components in the feedback controlled component addition controller 26, which may incorporate a mass flow controller, controls flowrate and pressure of the inert stream 20.

Figure 2:
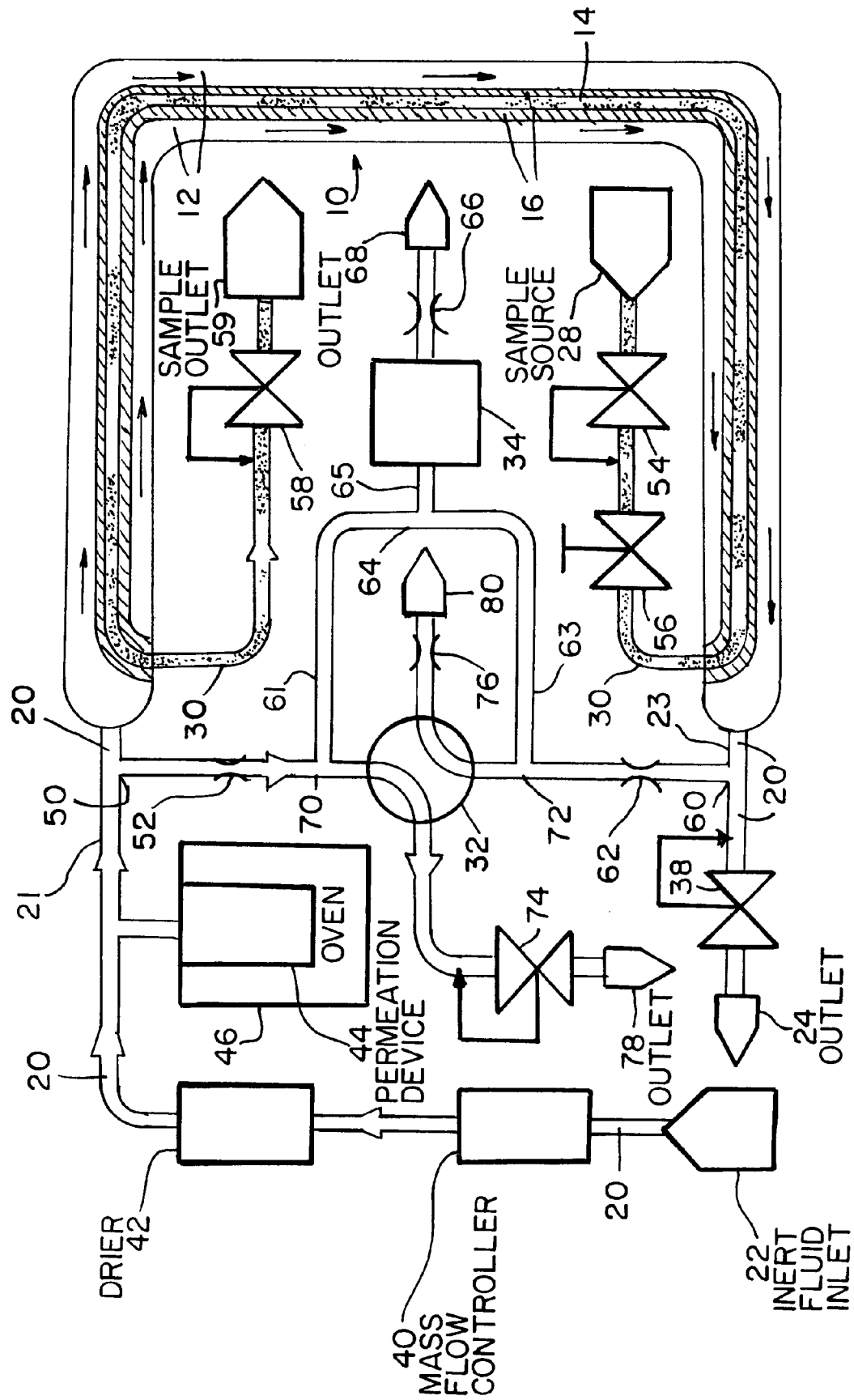
FIG. 2 is a detailed drawing of a preferred embodiment of a gas sampling and analyzing scheme of the invention.

FIG. 2 is a detailed drawing of a preferred embodiment of a gas sampling and analyzing scheme applied to hygrometry in corrosive gases. Inert stream inlet 22 provides a non-corrosive inert gas such as nitrogen to mass flow controller 40 followed by drier 42. A permeation device 44 adds moisture to the inert stream 20 downstream of the drier 42.

The permeation rate depends on temperature and pressure and is determined by weight loss over time prior to its use in this application. The temperature of permeation device 44 is controlled by placing it in an oven 46. The resulting concentration depends on the permeation rate and the size of the diluting flow set by the mass flow controller 42.

After moisture addition by the permeation device 44, part of the flow is split off in a tee 50 toward calibrated orifice 52, while the main stream continues into the exchange device 10. Sample stream 30 originates from source 28 which may be, e.g. a cylinder of corrosive gas. The sample stream 30 is pressure regulated by pressure regulator 54, passes through needle valve 56 and then enters the exchange device 10. The sample stream 30 leaves the exchange device 10 through back pressure regulator 58 and exits through sample stream outlet 59.

Inside exchange device 10, the wetted inert stream 20 in the chamber 12 is in contact with the sample stream 30 in the chamber 14 through a water permeable membrane 16. The inert stream 20 exits exchange device 10 into back pressure regulator 38 to leave through an inert stream outlet 24. Back pressure regulator 38 also provides the controlled pressure needed for the stable, reproducible operation of permeation device 44.

Another tee 60 between exchange device 10 and back pressure regulator 38 splits off a stream toward orifice 62. This orifice 62 is sized similarly as the orifice 52. Downstream, orifice 52 and orifice 62 are connected each to one of the legs 61, 63 of a tee 64 while the third leg 65 of tee 64 is connected to a sensor 34. Orifice 66 is positioned downstream of the sensor 34. After flow through or in contact with the sensor 34, the inert stream 20 leaves through outlet 68.

Two other tees, 70 and 72, are located respectively between orifice 52 and tee 64, and between orifice 62 and tee 64. From tees 70 and 72 gas flows toward the opposite legs of four way valve 32. The remaining two legs of four way valve 32 are connected to back pressure regulator 74 and to orifice 76.

Four way valve 32 takes either of two positions, the "downstream sampling position" or the "upstream sampling position." In the "downstream 23 sampling position", shown in FIG. 2, inert stream material from downstream of exchange device 10 is introduced to sensor 34. In the "upstream sampling position" the material has passed through orifice 52 and has not passed through exchange device 10.

In the downstream sampling position the inert stream material from tee 70 flows toward back pressure regulator 74 to exit through outlet 78. In this position a small part of the stream from tee 72 flows through orifice 76 to exit through outlet 80, while the main part flows to tee 64. At tee 64 a part of the inert stream splits off to sensor 34, while the remainder continues from tee 64 toward tee 70 where it blends in with the inert stream from orifice 52 to exit through back pressure regulator 74 and the outlet 78.

In the upstream sampling position, the inert stream from tee 72 flows through back pressure regulator 74 to exit through outlet 78. In this position, a small part of the stream from tee 70 flows through orifice 76 to exit through outlet 80, while the main part flows to tee 64. At tee 64 a part of the inert stream splits off to sensor 34, while the remainder continues from tee 64 toward tee 72 where it blends in with the inert stream flowing from orifice 62 to back pressure regulator 74.

The size of the flow through or in contact with sensor 34 is determined by its upstream pressure, which is set by back pressure regulator 74, the flow restriction created by orifice 66 together with that of sensor 34 and the pressure at outlet 68 downstream of orifice 66. The orifices are dimensioned such that the flowrates through orifice 62 as well as through orifice 52 each exceed the sum of the flowrate through the sensor 34 and the flowrate through orifice 76.

Inside exchange device 10 the sample stream flows through a relatively long tube of thin water permeable membrane 16. The inert gas stream 20 flows along the outside of membrane 16 in a direction counter to that of the sample stream 30. Exchange of moisture takes place through the wall of membrane 16 with, as a net result, a moisture concentration increase in the drier stream and a decrease in the wetter stream. The four way valve 32 switches periodically between monitoring inert stream 20 upstream 21 and downstream 23 of the membrane 16 and detects the result of the moisture exchange.

When the inert gas stream increases in moisture concentration after contact with the membrane 16, a feedback mechanism 36 (not shown in FIG. 2, but shown in FIG. 1) raises the moisture concentration upstream 21 of exchange device 10 by reducing the flowrate of the inert stream 20 through mass flow controller 40. Thus, the moisture added by permeation device 44 is less diluted and results in a higher concentration of moisture in inert stream 20. The reaction of the feedback mechanism 36 is proportional to the detected moisture concentration difference from sensor 34.

Alternatively, when the inert stream 20 decreases in moisture concentration after contact with the membrane 16, the feedback mechanism 36 decreases the moisture concentration upstream of exchange device 10 by increasing the flowrate of inert stream 20 through mass flow controller 40. Thus, the moisture added by permeation device 44 is more diluted and results in a lower concentration of moisture in inert stream 20.

The feedback mechanism 36 continues to adapt mass flow controller 40 and to move the system toward a state with no moisture concentration difference between the upstream and downstream sampling positions. Such state corresponds to an equal partial pressure of moisture in the sample stream 30 and the inert stream 20 inside the exchange device 10. Based on the fixed permeation rate (ng/minute) of device 44 and the flowrate (liter/minute) through mass flow controller 40, a calculation (division of a fixed number by the flowrate) results in the moisture concentration in the inert stream inside the exchange device 10. The partial pressures being equal, knowledge of the concentration in the inert stream 20 together with knowledge of the pressure of the sample gas 30 inside membrane 16 maintained by backpressure regulator 58 and knowledge of the pressure of the inert stream inside exchange device 10 maintained by backpressure regulator 38 allows the calculation of the concentration in sample gas 30, which is communicated to the user.

A preferred embodiment is according to FIG. 2 together with the previously described adaptation of the Perma Pure dryer with modifications according to the previously described preferred embodiment with the back pressure regulator 38 now connected to the shell port at the membrane extremity where the inert stream enters the first chamber and a flow restriction at the position where the back pressure regulator 38 used to be in the above description according to FIG. 2.

A preferred embodiment is according to the embodiment above but has the inert fluid stream that exits the back pressure regulator 38 teed in the inert fluid into the pressure controlling element 74 that controls the pressure of the inert fluid inside the target component sensor arrangement's pressure switch. This makes the flowrates from the two sample points in the first chamber into the target component sensor arrangement independently controllable from the pressure setting of the mentioned pressure controlling element 74.

A preferred embodiment has a feedback controlled component addition that splits the entering inert fluid stream into a first stream and a second stream where target component is added to the first stream and inert stream material is removed from the first stream in a controllable fashion where after the remainder of the first stream is teed in the second stream to become the feedback controlled component addition's output. This feedback controlled component addition is tunable from zero addition to an upper limit, where the upper limit occurs when no inert material is removed from the first stream while zero addition is accomplished when the flowrate of inert material removal from the first flow exceeds the flowrate of the first stream.

While the invention has been described with reference to specific embodiments, modifications and variations of the invention may be constructed without departing from the scope of the invention, which is defined in the following claims.

I claim:

1. A fluid sampling and analyzing apparatus for determining concentration of a target component in a sample fluid by creating a concentration of the target component in an inert fluid comprising:
   a) an exchange device having a first chamber and a second chamber where the first chamber has an inlet and an outlet and the second chamber has at least one opening;
   b) a membrane between the first chamber and the second chamber, wherein the membrane is selectively passable by the target component and forms a barrier for the inert fluid and the sample fluid;
   c) a target concentration sensor arrangement connected to the first chamber where the target concentration sensor arrangement comprises one or more sensors that are exposed to the inert fluid and the target component upstream of the inlet and downstream of the outlet; and
   d) an adjustable supply for changing concentration of the target component in the inert fluid upstream of the first chamber according to differences in target concentration in the inert fluid upstream and downstream of the first chamber sensed by the target concentration sensor arrangement.

2. The apparatus of claim 1, wherein the membrane is chemically resistant to the sample fluid.

3. The apparatus of claim 2, wherein the membrane is selected from the group consisting of semipermeable materials such as polyvinyl chloride, cellulose ccetate (Cellophane), Teflon, tracing cloth, Nylon and of ion-containing compounds such as perfluorosulfonate ionomer (Nafion), ethylenes, styrenes, rubbers, as well as compounds based on poly(tetrafluoroethylene).

4. The apparatus of claim 2, wherein the sample fluid is corrosive.

5. The apparatus of claim 1, wherein the concentration of the target component in the inert fluid is created at a level controlled by a signal from the target concentration sensor arrangement.

6. The apparatus of claim 5, wherein the target concentration sensor arrangement provides streams of inert fluid representative of the inert fluid upstream and downstream of a part of the membrane to a single sensor either by opening or closing valves on the flow path of such streams to the sensor or by rerouting such streams by valves at positions where the inert fluid flows away from the sensor.

7. The apparatus of claim 1, wherein the target concentration sensor arrangement provides streams of inert fluid representative of the inert fluid upstream and downstream of a part of the membrane to a single sensor either by opening or closing valves on the flow path of such streams to the sensor or by rerouting such streams by valves at positions where the inert fluid flows away from the sensor.

8. The apparatus of claim 1, wherein the membrane is selected from the group consisting of semipermeable materials such as polyvinyl chloride, cellulose acetate (Cellophane), Teflon, tracing cloth, Nylon and of ion-containing compounds such as perfluorosulfonate ionomer (Nafion), ethylenes, styrenes, rubbers, as well as compounds based on poly(tetrafluoroethylene).

9. The apparatus of claim 1, wherein the target component is moisture.

10. The apparatus of claim 1, wherein the exchange device is maintained at a stable temperature.

11. The apparatus of claim 1, wherein fluid pressures in the first chamber and the second chamber of the exchange device are maintained at stable values.

12. A method for determining the concentration range of a target component in a sample fluid by creating and measuring a concentration of the target component in an inert fluid comprising:
   a) providing an exchange device having a first chamber and a second chamber;
   b) providing a membrane between the first chamber and the second chamber that is selectively passable by the target component and is a barrier to the inert fluid and the sample fluid;
   c) flowing an inert fluid through the first chamber;
   d) filling the second chamber with the sample fluid;
   e) transferring the target component across the membrane from the first chamber to the second chamber and vice versa;
   f) providing a target concentration sensor arrangement connected to the first chamber where the target concentration sensor arrangement comprises one or more sensors that are exposed to the inert fluid upstream and downstream of the membrane;
   g) supplying target component to the inert stream upstream of the membrane;
   h) monitoring difference in sensor signals acquired upstream and downstream of the membrane by the target concentration sensor arrangement.

13. The method of claim 12, further comprising flowing the sample fluid through the second chamber.

14. The method of claim 13, wherein the membrane is chemically resistant to the sample fluid.

15. The method of claim 14, wherein the sample fluid is corrosive.

16. The method of claim 13, wherein the concentration of the target component in the inert fluid is created at a level controlled by the signals from the target concentration sensor arrangement until the target concentration in the inert fluid remains unchanged upstream and downstream of the membrane.

17. The method of claim 13, wherein the target concentration sensor arrangement provides streams of inert fluid representative of the inert fluid upstream and downstream of a part of the membrane to a single sensor either by opening or closing valves on the flow path of such streams to the sensor or by rerouting such streams by valves at positions where the inert fluid flows away from the sensor.

18. The method of claim 13, wherein the target component is moisture.

19. The method of claim 13, wherein the exchange device is maintained at a stable temperature.

20. The method of claim 13, wherein fluid pressures in the first chamber and the second chamber of the exchange device are maintained at stable values.

21. The method of claim 12, wherein the membrane is chemically resistant to the sample fluid.

22. The method of claim 21, wherein the sample fluid is corrosive.

23. The method of claim 12, wherein the concentration of the target component in the inert fluid is adjusted at a level controlled by the signals from the target concentration sensor arrangement until the target concentration in the inert fluid becomes equal upstream and downstream on the membrane.

24. The method of claim 12, wherein the target concentration sensor arrangement provides streams of inert fluid representative of the inert fluid upstream and downstream of a part of the membrane to a single sensor either by opening or closing valves on the flow path of such streams to the sensor or by rerouting such streams by valves at positions where the inert fluid flows away from the sensor.

25. The method of claim 12, wherein the membrane is selected from the group consisting of semipermeable materials such as polyvinyl chloride, cellulose acetate (Cellophane), Teflon, tracing cloth, Nylon and of ion-containing compounds such as perfluorosulfonate ionomer (Nafion), ethylenes, styrenes, rubbers, as well as compounds based on poly(tetrafluoroethylene).

26. The method of claim 13, wherein the membrane is selected from the group consisting of semipermeable materials such as polyvinyl chloride, cellulose acetate (Cellophane), Teflon, tracing cloth, Nylon and of ion-containing compounds such as perfluorosulfonate ionomer (Nafion), ethylenes, styrenes, rubbers, as well as compounds based on poly(tetrafluoroethylene).

27. The method of claim 12, wherein the target component is moisture.

28. The method of claim 12, wherein the exchange device is maintained at a stable temperature.

29. The method of claim 12, wherein fluid pressures in the first chamber and the second chamber of the exchange device are maintained at stable values.

* * * * *